United States Patent
Wolske

(10) Patent No.: US 8,316,649 B2
(45) Date of Patent: Nov. 27, 2012

(54) THERMAL CONTROLLED PILLOW

(75) Inventor: Bill Wolske, Newmarket (CA)

(73) Assignee: Superior Quilting Ltd., Toronto (CA)

( * ) Notice: Subject to any disclaimer, the term of this patent is extended or adjusted under 35 U.S.C. 154(b) by 232 days.

(21) Appl. No.: 11/972,646

(22) Filed: Jan. 11, 2008

(65) Prior Publication Data

US 2008/0168605 A1 Jul. 17, 2008

Related U.S. Application Data

(60) Provisional application No. 60/880,058, filed on Jan. 12, 2007.

(51) Int. Cl.
*F25B 21/02* (2006.01)
*F25B 27/00* (2006.01)
(52) U.S. Cl. .......................... 62/3.5; 62/238.2
(58) Field of Classification Search ............... 62/3.5, 62/3.7, 238.2, 261
See application file for complete search history.

(56) References Cited

U.S. PATENT DOCUMENTS

| | | | |
|---|---|---|---|
| 3,648,469 A | 3/1972 | Chapman | |
| 3,840,918 A | 10/1974 | Shave | |
| 4,325,151 A | 4/1982 | Wu | |
| 4,777,346 A | 10/1988 | Swanton, Jr. | |
| 4,847,931 A * | 7/1989 | Bard | 5/644 |
| 4,887,326 A | 12/1989 | O'Brien et al. | |
| 4,932,089 A | 6/1990 | Laviero | |
| 5,163,194 A | 11/1992 | Dixon | |
| 5,344,437 A | 9/1994 | Pistay | |
| 5,503,618 A | 4/1996 | Rey | |
| 5,545,199 A | 8/1996 | Hudson | |
| 5,562,604 A * | 10/1996 | Yablon et al. | 601/148 |
| 5,632,051 A | 5/1997 | Stanley et al. | |
| 5,916,088 A | 6/1999 | Gueli | |
| 6,256,818 B1 | 7/2001 | Hughes | |
| 6,412,975 B1 * | 7/2002 | Schuchardt et al. | 366/337 |
| 6,516,624 B1 | 2/2003 | Ichigaya | |
| 7,017,214 B2 | 3/2006 | Bard | |
| 2001/0004680 A1 * | 6/2001 | Brotz | 601/150 |
| 2002/0124317 A1 | 9/2002 | Schupp et al. | |
| 2003/0088300 A1 * | 5/2003 | Vester | 607/109 |
| 2005/0050636 A1 | 3/2005 | Setokawa | |
| 2005/0251919 A1 | 11/2005 | Bard | |
| 2006/0058587 A1 * | 3/2006 | Heimbrock et al. | 600/300 |
| 2006/0137358 A1 * | 6/2006 | Feher | 62/3.3 |

FOREIGN PATENT DOCUMENTS

| | | |
|---|---|---|
| EP | 1101429 A1 | 5/2001 |
| EP | 0789524 B1 | 5/2005 |
| JP | 54048350 A | 4/1979 |
| JP | 63277066 A | 11/1988 |
| JP | 01046454 A | 2/1989 |

(Continued)

*Primary Examiner* — Frantz Jules
*Assistant Examiner* — Emmanuel Duke
(74) *Attorney, Agent, or Firm* — Bereskin and Parr LLP/S.E.N.C.R.L., s.r.l.

(57) ABSTRACT

A thermal pillow apparatus comprising a pillow element, a heat exchanger, a thermal liquid, a fluid pump and a controller is disclosed. The thermal liquid circulates between the heat exchanger and the pillow element in a closed loop, transferring thermal energy between the heat exchanger and the pillow element. A fluid pump is disposed in the closed loop to aid in circulating the thermal liquid within the closed loop. A Peltier device is the typical heat pump element used in the heat exchanger. The controller coordinates the operation of the thermal pillow apparatus, for example monitoring the temperature of the thermal liquid, and activating the heat exchanger and the fluid pump.

18 Claims, 6 Drawing Sheets

| | FOREIGN PATENT DOCUMENTS | | |
|---|---|---|---|
| JP | 01129860 A | | 5/1989 |
| JP | 01145011 A | | 6/1989 |
| JP | 02182210 A | | 7/1990 |
| JP | 03087530 A | | 4/1991 |
| JP | 03272711 A | | 12/1991 |
| JP | 04183415 A | | 6/1992 |
| JP | 06-218004 | * | 8/1994 |
| JP | 06217854 A | | 8/1994 |
| JP | 06218004 A | | 8/1994 |
| JP | 07265348 A | | 10/1995 |
| JP | 07298971 A | | 11/1995 |
| JP | 07323041 A | | 12/1995 |
| JP | 08084744 A | | 4/1996 |
| JP | 08089383 A | | 4/1996 |
| JP | 08117076 A | | 5/1996 |
| JP | 08187151 A | | 7/1996 |
| JP | 08275966 A | | 10/1996 |
| JP | 08275967 A | | 10/1996 |
| JP | 08275968 A | | 10/1996 |
| JP | 08299140 A | | 11/1996 |
| JP | 08308704 A | | 11/1996 |
| JP | 08308869 A | | 11/1996 |
| JP | 09-084677 | * | 3/1997 |
| JP | 09075194 A | | 3/1997 |
| JP | 09084677 A | * | 3/1997 |
| JP | 09173193 A | | 7/1997 |
| JP | 09182766 A | | 7/1997 |
| JP | 09192161 A | | 7/1997 |
| JP | 10043023 A | | 2/1998 |
| JP | 10263003 A | | 10/1998 |
| JP | 10277080 A | | 10/1998 |
| JP | 11332713 A | | 12/1999 |
| JP | 2000201962 A | | 7/2000 |
| JP | 2001-070335 | * | 3/2001 |
| JP | 2001070335 A | | 3/2001 |
| JP | 2001078870 A | | 3/2001 |
| JP | 2001212168 A | | 8/2001 |
| JP | 2001252162 A | | 9/2001 |
| JP | 2001299538 A | | 10/2001 |
| JP | 2001309937 A | | 11/2001 |
| JP | 2002233442 A | | 8/2002 |
| JP | 2002272580 A | | 9/2002 |
| JP | 2002291790 A | | 10/2002 |
| JP | 2002330986 A | | 11/2002 |
| JP | 2003079655 A | | 3/2003 |
| JP | 2003299559 A | | 10/2003 |
| JP | 2004097491 A | | 4/2004 |
| JP | 2004350990 A | | 12/2004 |
| JP | 2005007116 A | | 1/2005 |
| JP | 2005087693 A | | 4/2005 |
| JP | 2005-124609 | * | 5/2005 |
| JP | 2006025956 A | | 2/2006 |
| JP | 2006051295 A | | 2/2006 |
| JP | 2006051335 A | | 2/2006 |
| WO | 9613186 A1 | | 5/1996 |
| WO | 0006006 A1 | | 2/2000 |
| WO | 2005110169 A1 | | 11/2005 |
| WO | WO2006045220 | * | 5/2006 |

* cited by examiner

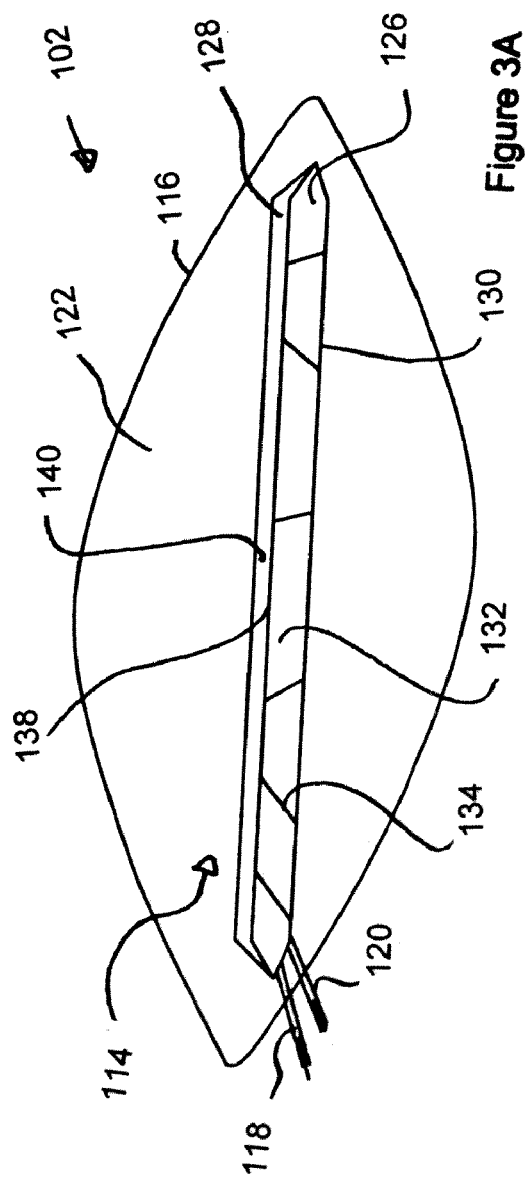
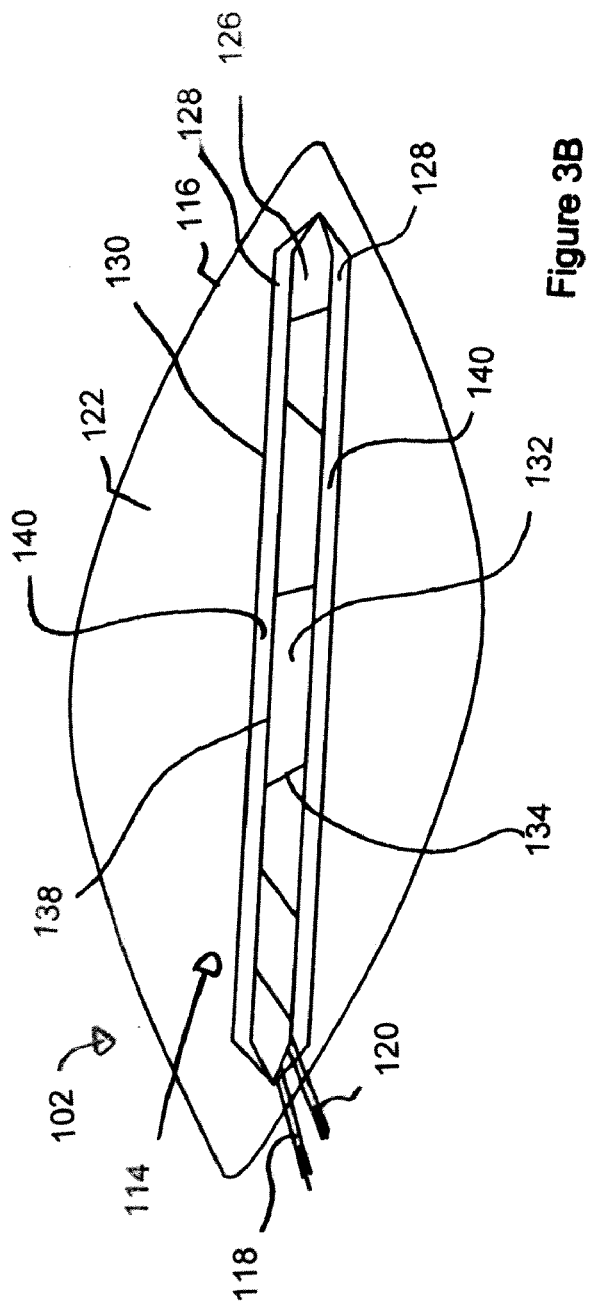
Figure 3A
Figure 3B

THERMAL CONTROLLED PILLOW

This is an application claiming the benefit under 35 USC 119(e) of U.S. Provisional Patent Application Ser. No. 60/880,058 filed Jan. 12, 2007. U.S. Ser. No. 60/880,058 is incorporated herein, in its entirety, by this reference to it.

FIELD OF THE INVENTION

The exemplary embodiments herein relate to a thermal controlled pillow. More particularly, the exemplary embodiments herein relate to a pillow using a thermoelectric heat pump to control the temperature of the pillow.

BACKGROUND OF THE INVENTION

A pillow can have a variety of uses. For example, a pillow is commonly used as a headrest or as a means of support while a user, such as a person, is lying down, or to permit a user to adjust their sitting position.

Amongst other reasons, a pillow can be used to increase the comfort level of a user. A pillow may also be used to support an ailing body part of the user. Having control of the thermal characteristics of the pillow, such as the temperature, can increase the comfort of the user. For example, a cool pillow may increase the quality of sleep of a user in a warm room, or a warm pillow may comfort a user sleeping in a cold room. Thermal control of a pillow can also help a user relieve the pain and discomfort of an ailing body part. For example, the application of cooling or heating may help relieve a user's discomfort from muscle or joint strain, headaches, chronic pain, poor circulation, etc.

In some pillows, hot or cold packs are used to adjust the thermal characteristics of a pillow. Alternatively, the pillow itself may be cooled or warmed. For example, a pillow may be placed in a freezer to reduce the overall temperature of the pillow. Problems with the use of hot or cold packs, or warming or cooling the pillow itself, include that the desired temperature of the pillow is not sustained.

Accordingly, there is a need for an improved thermal controlled pillow.

SUMMARY OF THE INVENTION

The exemplary embodiments described herein are directed to a thermal pillow apparatus comprising a pillow element, a heat exchanger, a thermal liquid, a fluid pump and a controller. The controller controls the operation of the heat exchanger to alter the thermal characteristics, for example heating or cooling, of the thermal liquid disposed in the heat exchanger. Typically, the heat exchanger includes a Peltier heat pump element, which pumps heat into or out of the thermal liquid disposed in the heat exchanger.

The pillow element also comprises a cushion element and a bladder, where the bladder comprises a first bladder chamber. The first bladder chamber is typically the component of the pillow element that is in fluid communication with the heat exchanger.

The controller also controls the operation of the fluid pump, where the fluid pump circulates the thermal liquid in a closed loop between the heat exchanger and the first bladder chamber; permitting heat transfer from the heat exchanger to the pillow element via the thermal liquid.

In another embodiment the thermal pillow apparatus includes a second bladder chamber that is thermally coupled to the first bladder chamber. The second bladder chamber typically comprises a gel.

In another example embodiment, the thermal pillow apparatus also comprises a control pendant that permits a user to interact and control the thermal pillow apparatus.

In one embodiment the fluid pump is adapted to continuously circulate the thermal liquid. In another embodiment, the fluid pump is adapted to intermittently circulate the thermal liquid, wherein the fluid pump circulates the thermal liquid when the heat exchanger is activated, and the fluid pump does not circulate the thermal liquid when the heat exchanger is not activated.

BRIEF DESCRIPTION OF THE DRAWINGS

For a better understanding of the present invention and to show more clearly how it may be carried into effect, reference will now be made, by way of example, to the accompanying drawings which show exemplary embodiments of the present invention, in which:

FIG. 3A is a sectional view of a first example embodiment of a pillow element of the thermal pillow apparatus of FIG. 1.

FIG. 3B is a sectional view of a second example embodiment of a pillow element of the thermal pillow apparatus of FIG. 1.

DETAILED DESCRIPTION OF THE INVENTION

Figure 1:
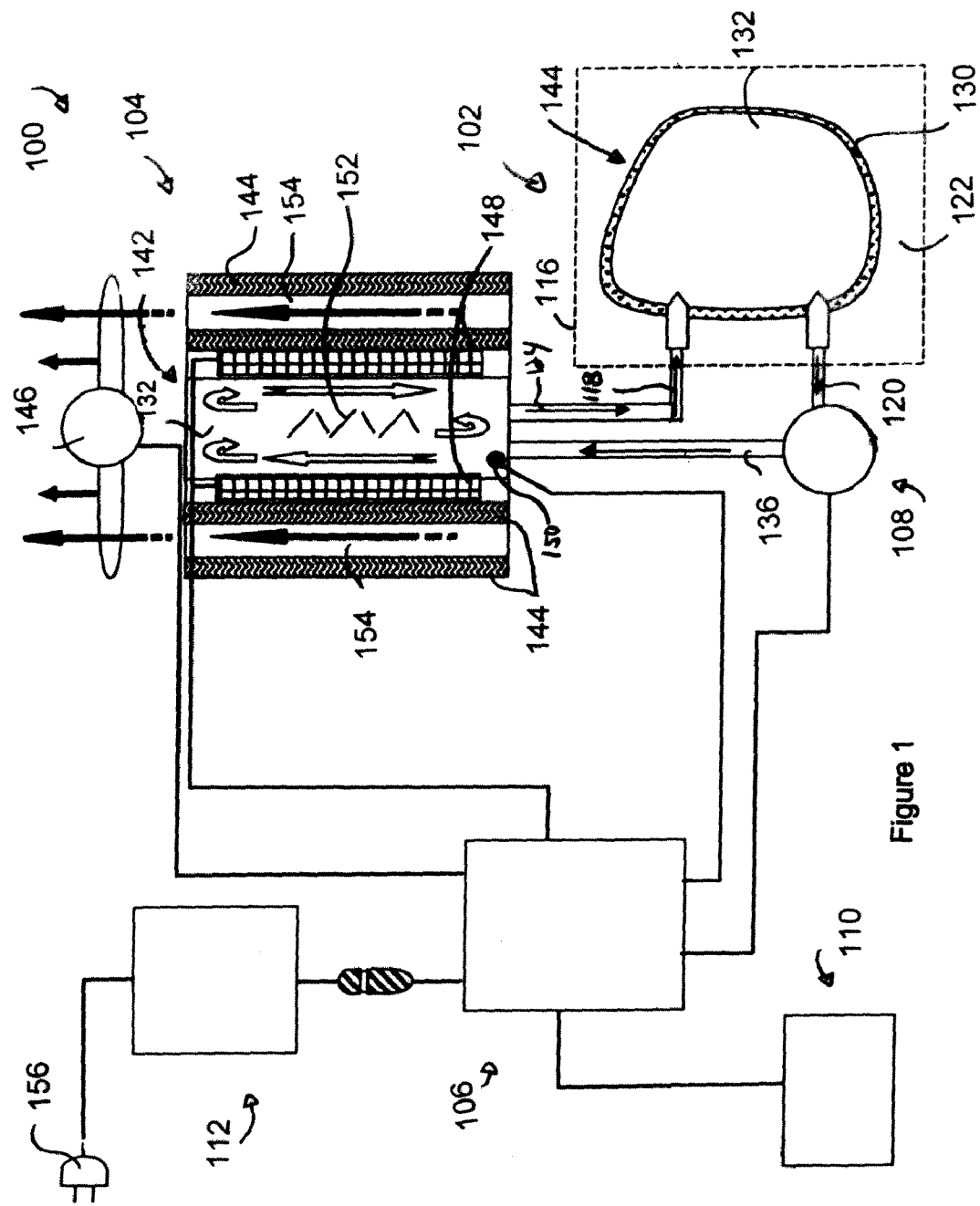
FIG. 1 is a schematic view of an exemplary embodiment of a thermal pillow apparatus.

Where considered appropriate, reference numerals may be repeated among the Figures to indicate corresponding or analogous elements.

Reference is first made to FIG. 1, which illustrates a first exemplary embodiment of a thermal pillow apparatus 100. The thermal apparatus 100 comprises a pillow element 102, a heat exchanger 104, a controller 106, a fluid pump 108, a control pendant 110, and a power supply 112.

Reference is now made to FIGS. 1, 2, 3A and 3B. Pillow element 102 comprises a cushion element 122, a bladder 114, an outer casing 116, a pillow element thermal liquid inlet 118 and a pillow element thermal liquid outlet 120. Although in the illustrated example embodiment only one bladder 114 is shown, it should be understood that more than one bladder 114 may also be used in pillow element 102. Pillow element 102 typically has an outer perimeter defined by the outer casing 116. The outer casing 116 may be made of material such as, for example, cotton, polyester, foam, memory foam or any fabric or material.

The outer casing 116 may be constructed, for example, as a sleeve that is sized to contain the bladder 114 and the cushion element 122. Alternatively, the outer casing 116 may be defined by the outer perimeter of the cushion element 122, or the outer casing 116 may be defined by a bladder outer wall element 130. A user may directly tactilely interact with the outer casing 116, for example by placing their head on the outer casing 116 when they are sleeping, or by placing the outer casing 116 adjacent to an area of chronic pain, such as, for example a lower back.

In addition, the outer casing 116 also typically comprises openings (not shown) adapted for the pillow element thermal liquid inlet 118, and the pillow element thermal liquid outlet 120. The openings (not shown) are usually dimensioned so that the pillow element thermal liquid inlet 118 and the pillow element thermal liquid outlet 120 can pass through the openings (not shown), permitting the pillow element thermal liquid inlet 118 and the pillow element thermal liquid outlet 120 to be in fluid communication with a first thermal liquid circulation conduit 124, and a second thermal liquid circulation conduit 136, respectively.

A person skilled in the art would understand that an additional layer or series of layers, such as, for example a pillowcase (not shown), could be placed onto the outer casing 116 of the pillow element 102 forming, for example, a further outer sleeve or outer boundary. Typically, if an additional material or sleeve is placed over the outer casing 116, the user tactilely interacts with the additional material or sleeve, and not the outer casing 116. A pillowcase may be used to facilitate cleaning the pillow element 102, where the pillowcase can be easily removed, washed and replaced.

In addition, the outer casing 116 may also be composed of a material or fabric that is simple to clean. Alternatively, the bladder 114, the pillow element thermal liquid inlet 118, and the pillow element thermal liquid outlet 120 may be removable from the outer casing 116 enabling simplified cleaning of the outer casing 116.

The cushion element 122 is typically located adjacent to the outer casing 116, and the bladder 114. Typically, the cushion element 122 is located between the outer casing 116 and the bladder 114. In the illustrated embodiment, the cushion element 122 covers substantially the entire bladder 114. The cushion element 122 may be composed of, for example, cotton batting, memory foam, open celled foam, closed cell foam, any mixture of the above, or any type of material typically used in a pillow. The cushion element 122 may, for example, provide a soft medium that may provide a level of comfort to a user, such as a person, as the user interacts with the pillow element 102. For example, the cushion element 122 may make the pillow element 102 comfortable for a user to place their head on the pillow element 102 when the user sleeps.

In some example embodiments, the pillow element 102 may not comprise a cushion element 122. For example, the pillow element 102 may comprise a bladder 114, an outer casing 116, a pillow element thermal liquid inlet 118 and a pillow element thermal liquid outlet 120.

The bladder 114 typically comprises a bladder outer wall 130, a first bladder chamber 126, and a second bladder chamber 128. In some example embodiments, the bladder 114 may be removable from the pillow element 102. The bladder 114 may be removed, for example, to facilitate cleaning of the bladder outer wall 130, or the cleaning of the cushion element 122, or cleaning of the outer casing 116, or to inspect and maintain the bladder 114.

The bladder outer wall 130 may be, for example, constructed of a liquid impermeable flexible material such as plastic or rubber suitable for use with the thermal liquid 132. For example, the bladder outer wall 130 may be water impermeable. The bladder outer wall 130 may also comprise a flocked surface (not shown). The flocked surface (not shown) may, for example, improve a user's ability to grip and interact with the bladder 130. The bladder outer wall 130 may also not comprise a flocked surface.

The bladder outlet wall 130 can deform as pressure is applied. For example, if a user places a load, such as for example their head, onto the pillow element 102, there may be a pressure applied to the bladder outer wall 130 causing the bladder outer wall 130 to deform in response to the pressure. Alternatively, a pressure applied to the interior of the bladder outer wall 130, from, for example, a hydrostatic pressure from the thermal liquid 132, may also cause the bladder outer wall 130 to deform.

The bladder outer wall 130 permits the transfer of thermal energy to and from the thermal liquid 132, typically located within the first bladder chamber 126. The thermal energy may be transferred, for example, to a user adjacent to the pillow element 102 who may be resting a body part against the pillow element 102. The thermal energy transferred may serve to cool or heat the user who is adjacent to the pillow element 102.

As mentioned, the bladder 114 comprises a first bladder chamber 126. Typically the first bladder chamber 126 is in fluid communication with the first and second thermal liquid circulation conduits 124, 136 through the pillow element thermal liquid inlet 118 and the pillow element thermal liquid outlet 120. Typically, the first bladder chamber 126 contains at least some thermal liquid 132. The first bladder chamber 126, aside from the pillow element thermal liquid inlet 118 and the pillow element thermal liquid outlet 120, is typically sealed such that the thermal liquid 132 cannot leak out. In another example embodiment the first bladder chamber 126 may include a resealable inlet (not shown) that permits a user to add, remove, or alter the thermal liquid 132 in the first bladder chamber 126.

The thermal liquid 132 may be comprised of, for example, water chlorinated water, water/propylene glycol or propylene glycol, any relatively inert fluid having suitable heat capacity and viscosity characteristics. The thermal liquid 132 may be selected, or may include an additive, to retard bacteria growth or to reduce damage to the pillow element 102, or other surrounding bedding material, should the bladder 114 spill or leak.

Thermal liquid 132 may be circulated from a heat exchanger 104 to the first bladder chamber 126 of the bladder 114 within pillow element 102 via the first thermal liquid circulation conduit 124. From the first bladder chamber 126, the thermal liquid 132 typically transfers thermal energy from or to a user who is adjacent to the pillow element 102. The thermal liquid 132 is then typically re-circulated to the heat exchanger 104 via a second thermal liquid circulation conduit 136. As such, the thermal liquid 132 operates in a closed loop between the heat exchanger 104 and the pillow element 102. A fluid pump 108, that is located within the closed loop in which the thermal liquid 132 circulates, typically circulates the thermal liquid 132 within the closed loop. The fluid pump 108 is discussed in more detail below.

In another example embodiment, the first bladder chamber 126 may also comprise a plurality of galleries 134. The galleries 134 may aid, for example, in directing and forcing circulation of the thermal liquid 132 within the first bladder chamber 126; including when a user is applying pressure to the pillow element 102 and therefore to the first bladder chamber 126, for example by a user placing their head on the pillow element 102. The galleries 134 may, for example, aid in ensuring a more uniform circulation of thermal liquid 132 in the first bladder chamber 126. The galleries 134 may also therefore ensure a more even transfer of thermal energy to and from the thermal liquid 132 located within the first bladder chamber 126.

The bladder 114 may also comprise a second bladder chamber 128. The second bladder chamber 128 is thermally coupled to the first bladder chamber 126. As illustrated in FIGS. 3A and 3B, the second bladder chamber 128 may be located adjacent to only one side of the first bladder chamber (FIG. 3A), or the second bladder element 128 may be located adjacent to both sides of the bladder chamber 128 (FIG. 3B). In another example embodiment (not shown) the pillow element 102 may comprise more than one bladder 114. Alternatively, in one example embodiment, the bladder 114 may comprise a plurality of second bladder chambers 128.

Typically, the second bladder chamber 128 is contained within the bladder outer wall 130. However the second bladder chamber 128 is separated from the first bladder chamber 126 by a bladder inner wall 138. The bladder inner wall 138 is therefore adjacent to both the first bladder chamber 126 and the second bladder chamber 128. In one example embodiment, illustrated in FIG. 3A, the bladder has a three-ply construction comprised of the top bladder outer wall 130, the bladder inner wall 138, and bottom bladder outer wall 130. At the outer edge of the bladder 114, the three-ply construction of the bladder 114 may have common specific bonding paths.

The bladder inner wall 138 is typically made of the same material as the bladder outer wall 130. The second bladder chamber 128 is fluidly sealed such that no liquid can enter or exit the second bladder chamber 128. In this embodiment in some examples it may be possible to change the material contained within the second bladder chamber 128. In another example embodiment, the second bladder chamber 128 may comprise an inlet (not shown) that has a removable sealable cap (not shown). In this example embodiment, a user can therefore selective access the contents of the second bladder chamber 128 by removing and replacing the removable sealable cap (not shown).

In this embodiment, the second bladder chamber 128 typically comprises a gel 140. The gel 140 may be a viscous fluid, or any other gelatinous material. The gel 140 may aid in regulating, for example evening out, the thermal profile of the thermal energy being transferred to or from the thermal liquid 132 in the first bladder chamber 126. The gel 140 may therefore, for example, keep the pillow element 102 from having portions that are of significantly different temperatures. The gel 140 may also aid in sustaining an even flow of thermal energy to and from the thermal liquid 132 in the first bladder chamber 126, even as the thermal characteristics of the thermal liquid 132 change.

Figure 2:
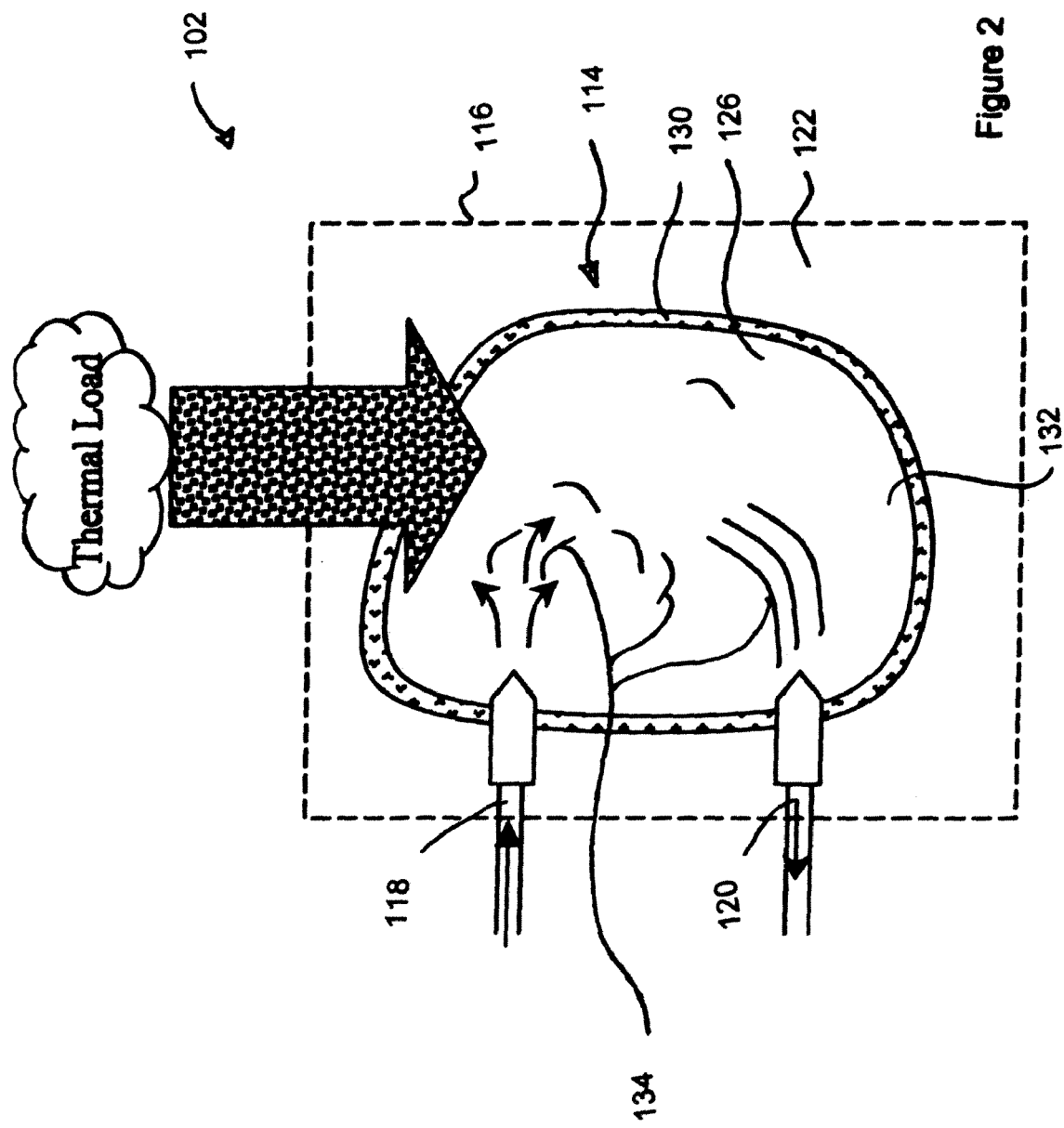
FIG. 2 is an isolated schematic view of a pillow element of the thermal pillow apparatus of FIG. 1.

Referring now to FIG. 2, a thermal load may be applied to the pillow element 102. The thermal load is typically the user, for example a user's head, being applied to the pillow element 102. The placement of a user's head introduces a source or sink of thermal energy to or from the pillow apparatus 102. The thermal source may thereafter transfer or receive thermal energy from the pillow element 102, through, as explained in greater detail above, the thermal energy transferred from the thermal liquid 132 through the bladder 114, the cushion element 122, and the outer casing 116 of the pillow element 102. Typically, the thermal load, such as the user's head or body part, is applied to the side of the pillow element 102 that is adjacent to the second bladder chamber 128. This may be only one side of the pillow element 102, as shown in FIG. 3A, or both sides of the pillow element 102 shown in FIG. 3B.

Figure 4:
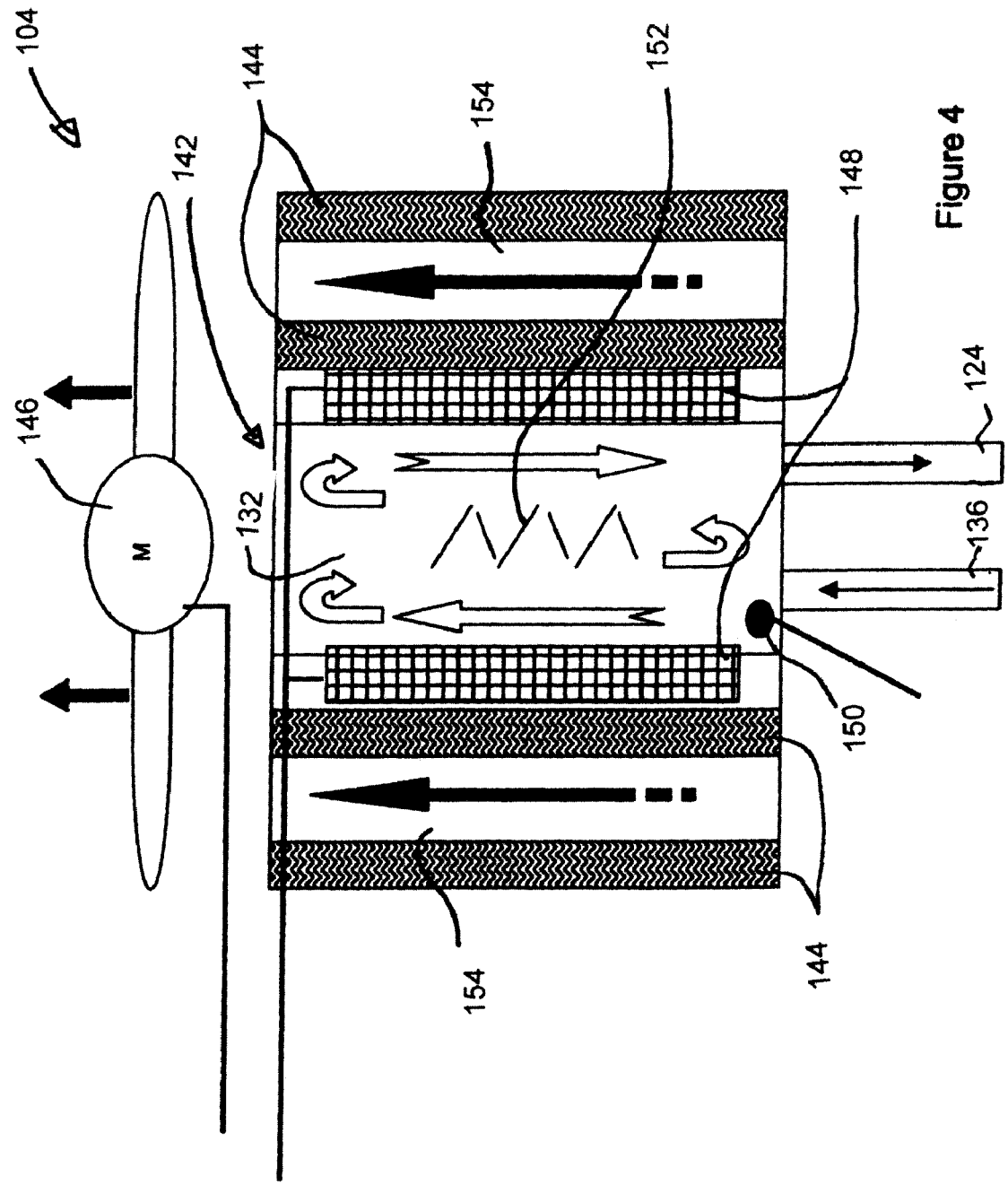
FIG. 4 is an isolated schematic view of a heat exchanger of the thermal pillow apparatus of FIG. 1.

Reference is now made to FIGS. 1 and 4, and specifically the heat exchanger 104. The heat exchanger 104 typically comprises a liquid to air heat exchanger chamber 142, a heat sink 144, a fan 146, a heat pump element 148, and a temperature sensor 150.

The liquid to air heat exchanger chamber 142 is fluidly sealed, with the exception of the liquid to air heat exchanger chamber 142 being in fluid communication with the first bladder chamber 126 via a first thermal liquid circulation conduit 124 and a second thermal liquid circulation conduit 136. The thermal liquid 132 circulates within the liquid to air heat exchanger chamber 142 contacting the static mixer elements 152, which aid in causing turbulent flow of the thermal liquid 132, which may increase the thermal transfer of the thermal liquid 132.

In addition, typically the liquid to air heat exchanger chamber 142 is of multi-pass design. For example, the thermal liquid 132 enters the liquid to air heat exchanger chamber 142 from the second thermal liquid circulation conduit 136, and passes through the liquid to air heat exchanger chamber 142 to the opposite end of the liquid to air heat exchanger chamber 142. The thermal liquid 132 then returns to the initial end of the liquid to air heat exchanger chamber 142. The thermal liquid may repeat this a number of times. Finally, the thermal liquid exits the liquid to air heat exchanger chamber 142 through the first thermal liquid circulation conduit 124. The multi-pass design may permit greater thermal energy transfer to and from the thermal liquid 132 within the heat exchanger 104.

In the present example embodiment, two heat pump elements 148 in series are used. The thermal liquid 132 within the liquid to air heat exchanger chamber 142 circulates adjacent to a surface of each of the heat pump elements 148. For example, a surface of each heat pump element 148 is mounted along the length of opposite sides of the liquid to air heat exchanger chamber 142. The heat pump element 148 can therefore transfer thermal energy to or from the thermal liquid 132, through this contact. The multi-pass design and turbulent flow of the thermal liquid within the liquid to air heat exchanger chamber 142 may enhance the transfer of thermal energy to and from the two heat pump elements 148 to the thermal liquid 132.

In the present example, the heat pump element 148 is a Peltier device; also commonly known as a thermoelectric heat pump. However, other types of heating pumps including, for example, a compressor based refrigeration or heating system may also be used.

A person skilled in the art would understand the function of a Peltier device. Using the Peltier device as the heat pump element 148, the thermal liquid 132 can be heated or cooled by the application of a current to the Peltier device. A Peltier device typically also operates with very little audible sound. In this exemplary embodiment the Peltier device is also typically relatively small in size and is therefore portable, permitting a user to easily move the Peltier device, or in this example the entire thermal pillow apparatus 100.

As mentioned, in the present example embodiment two Peltier devices in series are used. These Peltier devices are typically equally sized. Two Peltier devices used in series may reduce the current loading required. In addition, powering two Peltier devices at reduced voltages may, for example, result in better efficiency and a longer useful life of the Peltier devices.

The heat pump elements 148 are usually thermally coupled to a heat sink 144. Typically, because two heat pump elements 148 are used, two heat sinks 144 are used as well, in order to aid in the dispersion or gathering of the thermal energy transferred to or from the heat pump 148. Typically, a Peltier type heat pump element 148 has two surfaces, a cold surface and a hot surface, with the Peltier device "pumping" heat from one surface to the other through the application of a current.

In the present embodiment, the heat sink 144 may form one surface of the Peltier device, or it may be thermally coupled to one surface of the Peltier device. The heat pump element 148 then forms the other surface. Switching the direct of current flow in the Peltier device reverses which surface is warm or cold. The heat sink 144 thermally coupled to the Peltier device therefore typically transfers thermal energy to or from the heat pump element 148 into the atmospheric air. In the present example embodiment, the surface area of the heat sink 144 exposed to the atmosphere is increased through a heat sink cavity 154. The greater surface area of the heat sink 144 resulting from the heat sink cavity 154 may permit increased heat transfer to or from the heat sink 144 into the atmosphere.

In the present example embodiment, the heat exchanger 104 also includes a fan 146. Typically the fan 146 comprises an electric motor. In this example the fan 146 is operably coupled to the controller 106. The fan 146 may increase the airflow passing over the heat exchanger 104, and particularly over the surface area of the heat sinks 144 and the heat sink cavities 154. The increased airflow over the heat sinks 144 can increase the thermal transfer to or from the heat sink 144.

In this example, a temperature sensor 150 is also coupled to the heat exchanger 104. In this embodiment the temperature sensor 150 is thermally coupled to the liquid to air heat exchanger chamber 142. The temperature sensor 150 may, however, be thermally coupled to any other location, for example on the first thermal liquid circulation conduit 124, second thermal liquid circulation conduit 136, the heat pump element 148, the heat sink 144, the first bladder chamber 126, or the second bladder chamber 128. The temperature sensor 150 may be, for example a thermistor. The temperature sensor 150 is also typically operably coupled to the controller 106.

A condensation wick (not shown) may also be included in the heat exchanger 104. For example, the condensation wick may be mounted adjacent to the heat sinks 144 and the heat pump elements 148. In this example, the condensation wick may form an insulating layer between the heat sinks 144 and the heat pump elements 148. The ends of the condensation wicks (not shown) may be coupled to the fluid pump 108 to aid, for example, in absorbing condensate that may form on the condensation wicks. Alternatively, if the condensation wicks are not used, the heat exchanger 104 may still use an insulation layer (not shown) between the heat pump 148 and the heat sink 144. The insulation layer typically reduces the unwanted transfer of thermal energy between the heat pump element 148 and the heat sink 144.

Although the above example embodiments describe a heat exchanger 104 with two heat pump elements 148 and two heat sink elements 144, other examples may only include one heat pump element 148 and/or one heat sink element 144 are also possible. In addition, examples including the use of three or more heat pumps 148 and/or three or more heat sinks 144 are also possible.

Reference is now made again to FIG. 1. The fluid pump 108 circulates the thermal liquid 132 in the closed loop between the first bladder chamber 126, and the heat exchanger 104. The pump 108 may be located anywhere in the closed loop. In the present exemplary embodiment the fluid pump 108 is in fluid communication with the second thermal liquid circulation conduit 136 and the pillow element thermal liquid outlet 120.

The fluid pump 108 is operably coupled to the controller 106. The controller may, for example, control the operation of the fluid pump 108. Depending on the control exerted by the controller 106, the fluid pump 108 may operate constantly, constantly circulating the thermal liquid 132 in the closed loop. Constant circulation of the thermal liquid 132 may help maintain the thermal liquid 132 at a substantially equal thermal energy level within the closed loop.

Alternatively, the fluid pump 108 may only operate when the heat exchanger 104, or heat pump element 148 is in operation. The intermittent operation of the fluid pump 108 during the on-cycle of the heat exchanger 104 may be used to circulate the thermal liquid 132 when thermal transfer from the heat exchanger 104 to the pillow element 102 is desired. For example, when the user activates the heat exchanger 104 the fluid pump 108 is activated, however if the heat exchanger is not activated the fluid pump does not circulate the thermal liquid 132.

The fluid pump 108 may be any pump, however in this exemplary embodiment, an induction pump (not shown) may be used. The fluid pump 108 may, for example have a flow rate of 15-30 milliliters per second. The fluid pump 108 may comprise a direct current drive electric motor (not shown). In this embodiment the fluid pump 108 may be operated at a reduced speed than those permitted by the design of fluid pump 108. This may, for example, lead to a reduced peak current requirement, reduced noise levels, and extended pump/motor service life.

Reference is once again made to FIG. 1. The power supply 112 supplies power to the controller 106, which in turn provides power to the various components of the thermal pillow apparatus 100.

In this example, the power provided to the power supply 112 may come from the use of a battery (not shown) or a wall plug 156, or a combination of the two. In addition, the power supply 112 is typically designed to regulate its power output to be appropriate for the controller 106.

Alternatively, other power points, such as a car power point, for example a cigarette lighter, may also be used to provide power to the power supply 112. In these examples, the use of a battery (not shown) or a car power point (not shown) may permit the thermal pillow apparatus 100 to be portable. Whereas the use of a wall plug 156 is typically used for the stationary use of the pillow, for example at home or at a hotel room.

Reference is once again made to FIG. 1. In this example, the controller 106 is operably coupled to the power supply 112, the control pendant 110, the fluid pump 108, the heat exchanger fan 146, the heat pump 148, and the temperature sensor 150.

The controller 106 may be an integrated microcontroller that controls the components of the thermal pillow apparatus 100 operably linked to the controller 106. Alternatively, any type of thermo-state controller could be used. For example, a PLA, a PLC or any other type of control device. In one example embodiment, the controller 106 may be mounted to the heat exchanger 104, in a location where atmospheric air can flow freely over the surface of the controller 106.

As mentioned above, in this example the controller 106 receives power from the power supply 112. The controller 106 in turn uses that power to power itself, and to power various components of the thermal pillow apparatus 100.

The controller 106 is also operably linked to the control pendant 110. The control pendant 110 is an input interface that permits a user to control the operation of the controller 106. More discussion on the operation of the control pendant 110 is found below.

The controller 106 is also operably linked to the temperature sensor 150. The controller 106 can typically process the temperature sensed at the temperature sensor 150 and then, based on the user inputs through the control pendant 110, based on a default setting or internal algorithm, control the operation of the heat exchanger fan 146, the heat pump 148 and the fluid pump 108.

In one example, the user may adjust the desired temperature of the pillow element 102 through the control pendant 110. The controller 106 may, for example, cause the heat pump 148 to operate causing the addition or removal of thermal energy to the thermal liquid 132 in the liquid to air heat exchanger chamber 142. In addition, the controller may also cause the heat exchanger fan 146 to begin operating to aid in the removal of thermal energy from the heat sinks 144. The controller 106 may also cause the fluid pump 108 to operate, circulating the thermal liquid 132 in the closed loop between the bladder 114 and the heat exchanger 104. The circulated thermal liquid 132 then, through the process of heat transfer, discussed above, begins to transfer thermal energy to or from the pillow element 102, as was desired by the user. This is only one example, among many, of the operation of the controller 106.

Reference is now made to FIGS. 1, 5A, 5B and 5C, showing example embodiments of a control pendant 110. Where considered appropriate, reference numerals may be repeated among the Figures to indicate corresponding or analogous elements.

The control pendant 110 is operably linked to the controller 106, and permits a user to provide inputs to control, manipulate and monitor the operation of the controller 106, and therefore the thermal pillow apparatus 100. The control pendant 110 may be operably linked to the controller via a physical link, such as, for example, a wire or cable. Alternatively, the control pendant 110 may be operably linked to the controller via wireless technology, such as, for example, blue tooth technology or Wi-Fi.

The control pendant 110 typically includes a button, and may also include a plurality of buttons, and also may include a display or a plurality of displays. The buttons may include a temperature selector button 164, an activate button 166, and a mode selection button 168. A display may comprise a single light indicator, such as the selectable temperature setting display 158. The display may also, or alternatively, comprise a digital read out display, such as the temperature display 160, or the time display 162.

Figures 5A, 5B:
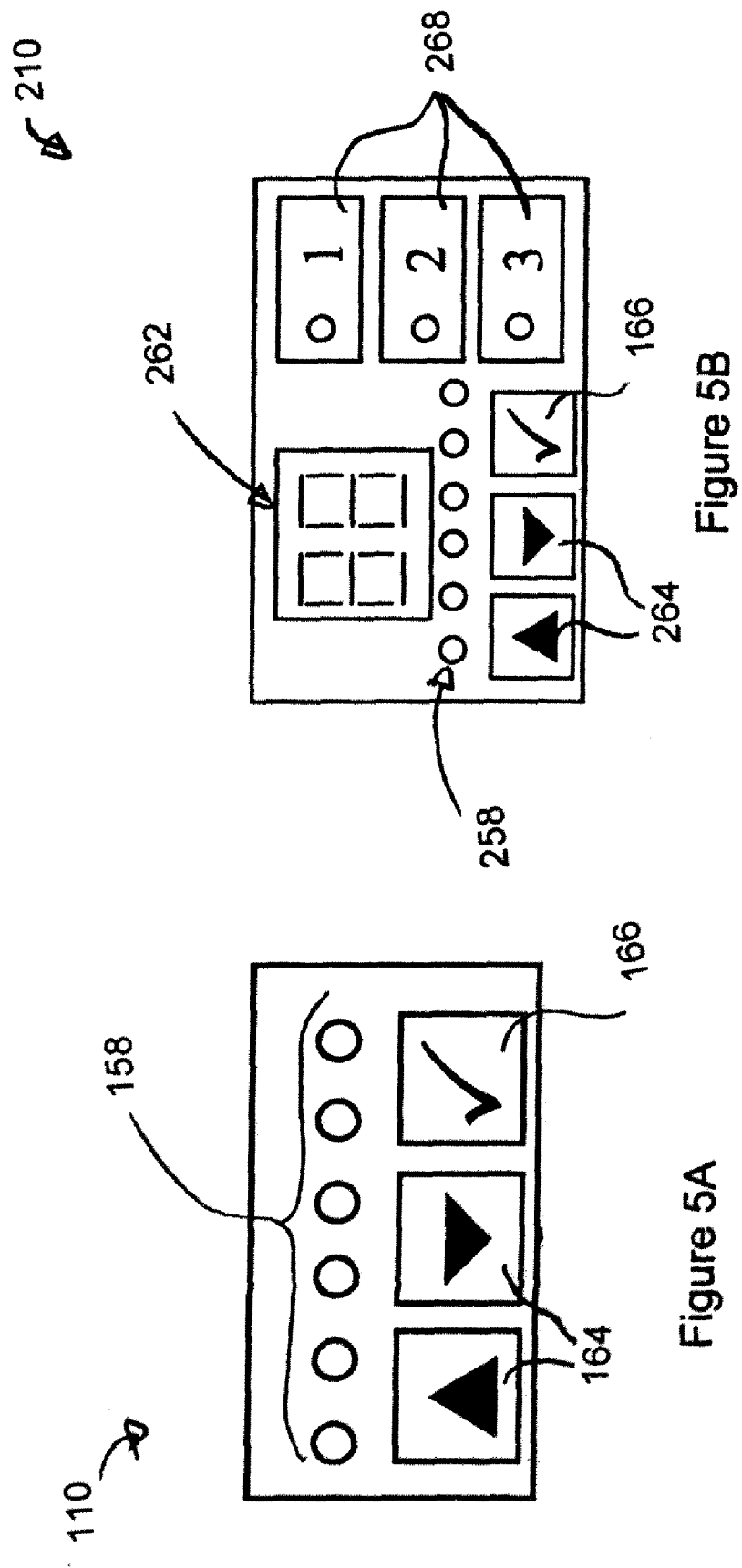
FIG. 5A is an isolated schematic view of a first example control pendant of the thermal pillow apparatus of FIG. 1.
FIG. 5B is an isolated schematic view of a second example control pendant of the thermal pillow apparatus of FIG. 1.

Reference is first made to FIG. 5A. In this embodiment the user may select between 6 preset temperatures for the thermal liquid 132, and in turn the pillow element 102. By pressing the temperature selector buttons 164, the user can choose their desired thermal liquid 132 temperature of choice. There may be, for example, 6 choices such as, for example, 5, 8, 12, 16, 30 or 35 degrees Celsius. Alternatively, the temperatures could also be in Fahrenheit. As the user selects a temperature setting, it is displayed by the illumination of one of the plurality of selectable temperature setting displays 158.

Once the temperature is selected (this temperature is known as a "set point"), the user may activate the operation of a heating/cooling cycle of the thermal pillow apparatus 100, by pressing the activate button 166, which in turn activates the controller 106. The controller 106 then activates the heat exchanger 104, including the heat pump elements 144 and possibly the fan 146, and typically the fluid pump 108. The heat pump elements 144 begin to transfer thermal energy to or from the thermal liquid 132 to achieve the user's desired temperature. The fluid pump 108 then, in turn, begins to circulate the thermal liquid 132 within the closed loop to the bladder 114 and therefore the pillow element 102.

Once the desired temperature of the thermal liquid 132 is achieved (as sensed by the temperature sensor 150), the controller 106 operates, as required, the various components of the thermal pillow apparatus 100 to sustain the temperature of the thermal liquid 132 for a single cycle. A cycle may be, for example, 20 minutes. A cycle may include a period of thermal transfer, followed by a period of no thermal transfer. For example, the cycle may include heating or cooling, and no heating or cooling. Once the time interval for a single cycle has elapsed, the controller 106 stops all operations, until the user reactivates the thermal pillow apparatus 100 by pressing the activate button 166 again.

Reference is now made to FIG. 5B. The control pendant in FIG. 5B is similar to the control pendant in FIG. 5A, however in this example a mode selection button 268 and a time display 262 are also added. In this example embodiment, the user can select between three modes of operation. The first mode, a single cycle mode, was described above with regard to FIG. 5A. The second mode allows the user to select a continuous cycle where after the first cycle has elapsed, a second cycle is automatically activated, and the controller 106 operates to sustain the temperature of the thermal liquid 132 at the desired temperature for a second cycle. This can continue for a pre-determined number of cycles, or perpetually until deactivated by the user. The user may, for example, deactivate the thermal pillow apparatus 100, by pressing the activate button 166 again. The time display 262 displays, for example the time remaining, or the time elapsed in the cycle.

As was discussed above, the cycle may include a period of thermal transfer followed by a period of non-thermal transfer. In a continuous cycle this may result in regularly repeating intervals of thermal transfer (for example heating or cooling), and regular repeating intervals of non-thermal transfer (a return to ambient conditions).

The third mode is similar to the second mode in that the third mode is a continuous cycle mode, however the third mode also permits two set points. For example, the user may enter a first and second set point. Once the set points are entered and the thermal pillow apparatus 100 is activated, the controller 106 operates to establish and maintain temperature of the thermal liquid 132 at the first set point (original desired temperature) for a preset amount of time, for example 1 cycle, or for a user entered amount of time. Following the passage of that amount of time, the controller 106 then establishes and maintains the temperature of the thermal liquid 132 at the second set point (second desired temperature). The controller 106 then maintains the thermal liquid 132 at the second set point, for a preset amount of time, for example 1 cycle, or for a user entered amount of time. In a continuous cycle, the thermal pillow apparatus 100 may repeat the above third mode, including operating at the first and second set point for a preset amount of time or cycles, or in perpetuity until deactivated by the user. Alternatively, the third mode may use a single cycle.

Figure 5C:
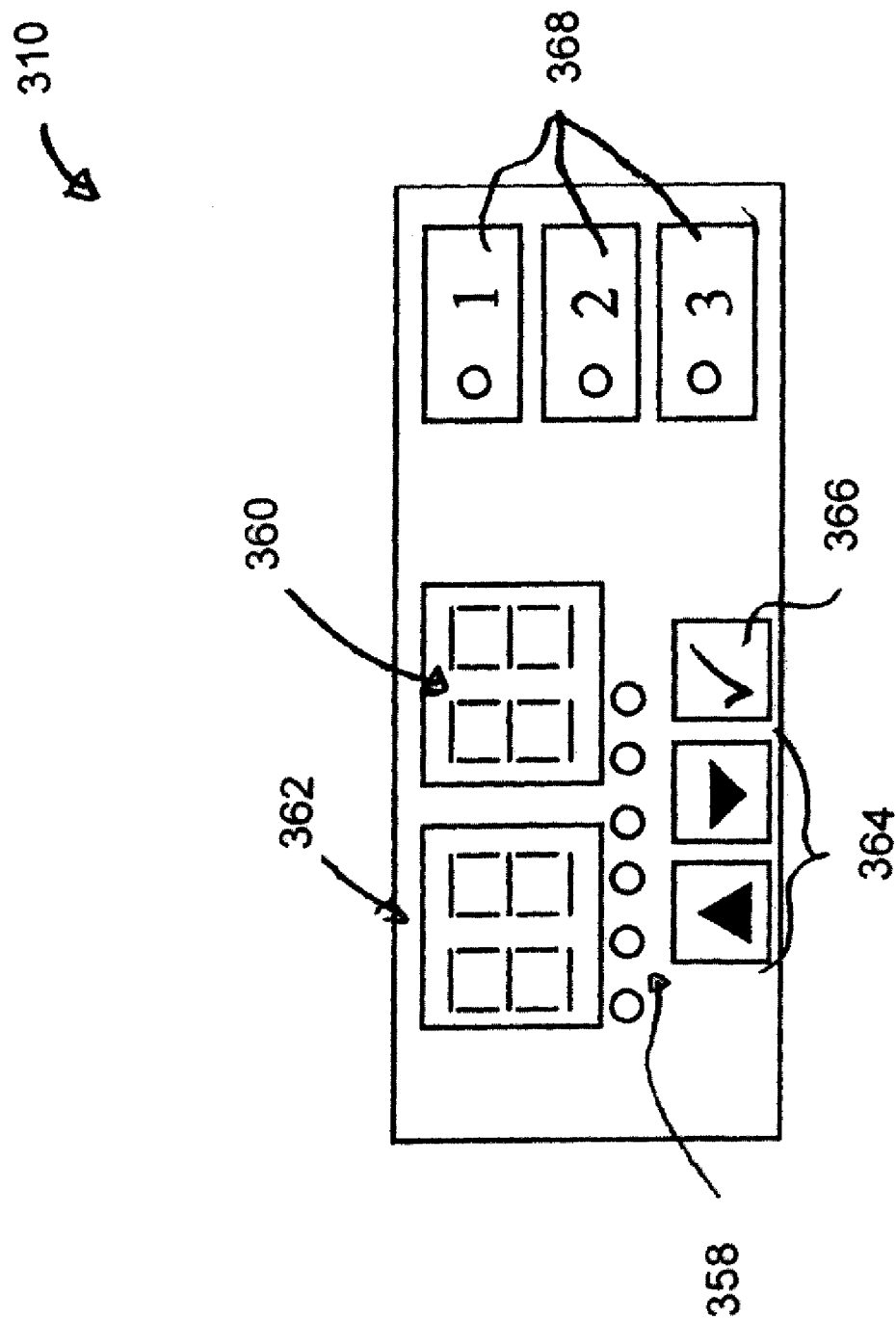
FIG. 5C is an isolated schematic view of a third example control pendant of the thermal pillow apparatus of FIG. 1.

Reference is now made to FIG. 5C, which illustrates a third example control pendant 310. Control pendant 310 is very similar to control pendant 110 and 210, however it also comprises a temperature display 360. In addition, to the features of control pendant 210, the control pendant 310 also permits a user to control the desired temperature in two ways. The first way is similar to that outlined for FIG. 5A, i.e. the, for example, six preset temperature values. However, control pendant 310, together with controller 306 also permit the user to enter the desired temperature of the thermal liquid 132 in 1 degree Celsius or Fahrenheit increments. For example, the user is not restricted to the values of 5, 8, 12, 16, 30 and 35 degrees Celsius, but may select any values at an increment of 1 degree Celsius or Fahrenheit.

The controller 306 operates the thermal pillow apparatus 100, as described above in the context of control pendant 110 and 210 to achieve the desired 1 degree temperature increment value. The 1 degree increment temperature values of the thermal liquid 132 can be achieved using a single cycle, or a continuous cycle with one set point or two set points, as described for other example embodiments.

While what has been shown and described herein constitutes one exemplary embodiment of the subject invention and while some variations of the embodiment have also been described, it should be understood that various modifications and adaptations of such embodiments can be made without departing from the present invention, the scope of which is defined in the appended claims.

The invention claimed is:

1. A thermal pillow apparatus comprising: a) a pillow element comprising a cushion element and a bladder, wherein the bladder includes a first bladder chamber and a bladder outerwall, and the cushion element is external the first bladder chamber and covers the entire bladder outerwall; b) a heat exchanger including a Peltier-type heat pump element, wherein the heat exchanger is in fluid communication with the first bladder chamber; c) a thermal liquid, wherein the thermal liquid can flow between the first bladder chamber and the heat exchanger in a closed loop; d) a fluid pump for circulating the thermal liquid in the closed loop; and e) a controller, wherein the controller is operably linked to the heat exchanger thereby regulating the temperature of the thermal liquid.

2. The thermal pillow apparatus of claim 1 wherein the first bladder chamber includes galleries.

3. The thermal pillow apparatus of claim 1 wherein the first bladder chamber includes a resealable inlet to add, remove, or alter the thermal liquid in the first bladder chamber.

4. The thermal pillow apparatus of claim 1 wherein the bladder comprises a second bladder chamber, and wherein the second bladder chamber is thermally coupled to the first bladder chamber.

5. The thermal pillow apparatus of claim 4 wherein the second bladder chamber comprises a gel.

6. The thermal pillow apparatus of claim 5 wherein the second bladder chamber includes a resealable inlet to add, remove, or alter the gel in the second bladder chamber.

7. The thermal pillow apparatus of claim 1 wherein the fluid pump is adapted to continuously circulate the thermal liquid.

8. The thermal pillow apparatus of claim 1 wherein the fluid pump is adapted to intermittently circulate the thermal liquid, wherein the fluid pump circulates the thermal liquid when the heat exchanger is activated, and the fluid pump does not circulate the thermal liquid when the heat exchanger is not activated.

9. The thermal pillow apparatus of claim 1 further comprising a control pendant operably linked to the controller, wherein a user can interact with the control pendant.

10. The thermal pillow apparatus of claim 9 wherein the control pendant is operably linked to the controller by a wire.

11. The thermal pillow apparatus of claim 9 wherein the control pendant is wirelessly operably linked to the controller.

12. The thermal pillow apparatus of claim 1 further comprising a power supply, wherein the power supply is operably linked to the controller.

13. The thermal pillow apparatus of claim 1 further comprising a pillowcase, wherein the pillow element is contained within the pillowcase.

14. The thermal pillow apparatus of claim 1 wherein the heat exchanger comprises a liquid to air heat exchanger chamber and wherein the liquid to air heat exchanger chamber includes static mixer elements.

15. The thermal pillow apparatus of claim 1 further comprising a condensation wick.

16. The thermal pillow apparatus of claim 4 wherein the second bladder chamber is contained within the bladder outer wall.

17. The thermal pillow apparatus of claim 4 wherein the second bladder chamber fluidly sealed.

18. The thermal pillow apparatus of claim 1 further comprising a temperature sensor in thermal communication with the thermal liquid.

* * * * *